(12) United States Patent
Knebel (10) Patent No.: US 6,977,724 B2
(45) Date of Patent: Dec. 20, 2005

(54) METHOD FOR SPECTRAL ANALYSIS, AND SCANNING MICROSCOPE

(75) Inventor: Werner Knebel, Kronau (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 182 days.

(21) Appl. No.: 10/393,607

(22) Filed: Mar. 21, 2003

(65) Prior Publication Data

US 2003/0179372 A1  Sep. 25, 2003

(30) Foreign Application Priority Data

Mar. 23, 2002 (DE) ................ 102 13 187

(51) Int. Cl.$^7$ ............................ G01N 21/64; G01J 3/06
(52) U.S. Cl. .................. 356/317; 356/308; 356/326; 250/458.1
(58) Field of Search .................. 356/308, 320, 356/326, 328, 331, 334, 317, 318, 417; 250/458.1, 250/459.1, 461.1, 461.2

(56) References Cited

U.S. PATENT DOCUMENTS

| 3,460,892 | A | * | 8/1969 | Dolin | .......................... 356/308 |
| 5,751,417 | A | | 5/1998 | Uhl | |
| 2001/0046046 | A1 | | 11/2001 | Schoeppe | |
| 2002/0021440 | A1 | | 2/2002 | Knebel | ........................ 356/308 |

FOREIGN PATENT DOCUMENTS

| DE | 4330347 | 3/1995 |
| DE | 19510102 | 2/1996 |
| DE | 19906757 | 2/1999 |
| DE | 19842288 | 2/2000 |
| DE | 10038049 | 2/2002 |
| WO | 0031577 | 6/2000 |

* cited by examiner

Primary Examiner—F. L. Evans
(74) Attorney, Agent, or Firm—Davidson, Davidson & Kappel, LLC (57) ABSTRACT

A method for spectral analysis of the light proceeding from a specimen using a multi-band detector comprises the steps of defining an overall spectral region; from the overall spectral region, defining a first spectral subregion and defining at least a second spectral subregion; simultaneously detecting the light proceeding from the specimen in the first and the second spectral subregion, and generating detection values; displacing the first spectral subregion and displacing the second spectral subregion within the overall spectral region; and repeating steps c) and d) until the light has been detected over the entire overall spectral region.

17 Claims, 5 Drawing Sheets

METHOD FOR SPECTRAL ANALYSIS, AND SCANNING MICROSCOPE

CROSS REFERENCE TO RELATED APPLICATIONS

This application claims priority of the German patent application 102 13 187.2 which is incorporated by reference herein.

FIELD OF THE INVENTION

The invention concerns method for spectral analysis of the light proceeding from a specimen using a multi-band detector.

The invention further concerns a scanning microscope having a multi-band detector that detects the light proceeding from a specimen in at least a first and a second spectral subregion.

BACKGROUND OF THE INVENTION

Spectral analysis of the light proceeding from a specimen plays a very important role in many fields of specimen examination, in particular in fluorescence microscopy and in confocal scanning microscopy.

In scanning microscopy, a specimen is illuminated with a light beam in order to observe the reflected or fluorescent light emitted from the specimen. The focus of an illuminating light beam is moved in a specimen plane by means of a controllable beam deflection device, generally by tilting two mirrors; the deflection axes are usually perpendicular to one another, so that one mirror deflects in the X direction and the other in the Y direction. Tilting of the mirrors is brought about, for example, by means of galvanometer positioning elements. The power level of the light coming from the specimen is measured as a function of the position of the scanning beam. The positioning elements are usually equipped with sensors to ascertain the present mirror position.

In confocal scanning microscopy specifically, a specimen is scanned in three dimensions with the focus of a light beam.

A confocal scanning microscope generally comprises a light source, a focusing optical system with which the light of the source is focused onto an aperture (called the "excitation pinhole"), a beam splitter, a beam deflection device for beam control, a microscope optical system, a detection pinhole, and the detectors for detecting the detected or fluorescent light. The illuminating light is coupled in via a beam splitter. The fluorescent or reflected light coming from the specimen travels back through the beam deflection device to the beam splitter, passes through it, and is then focused onto the detection pinhole behind which the detectors are located. Detected light that does not derive directly from the focus region takes a different light path and does not pass through the detection pinhole, so that a point datum is obtained which results, by sequential scanning of the specimen, in a three-dimensional image. A three-dimensional image is usually achieved by acquiring image data in layers, the track of the scanning light beam on or in the specimen ideally describing a meander (scanning one line in the X direction at a constant Y position, then stopping the X scan and stewing by Y displacement to the next line to be scanned, then scanning that line in the negative X direction at constant Y position, etc.). To permit acquisition of image data in layers, the specimen stage or the objective is displaced after a layer has been scanned, and the next layer to be scanned is thus brought into the focal plane of the objective.

German Unexamined Application DE 43 30 347 discloses an apparatus for the selection and detection of at least two spectral regions of a light beam, and the use of that apparatus in particular in a confocal scanning microscope. The apparatus has a selection device and a detection device, and for reliable simultaneous selection and detection of different spectral regions at high yield and with a simple design is configured in such a way that the selection device encompasses means for spectral dispersion of the light beam and means on the one hand for blocking out a first spectral region and on the other hand for reflecting at least one portion of the unblocked spectral region, and the detection device encompasses a first detector arranged in the beam path of the blocked-out first spectral region and a second detector arranged in the beam path of the reflected spectral region.

German Patent DE 195 10 102 C2 discloses an arrangement for confocal fluorescence microscopy in which an objective arrangement for acquiring an image of a specimen to be examined, at least one scanner mirror arranged after the objective arrangement, a tube lens, a confocal strip aperture, a first spectrometer arrangement, a wavelength selection aperture for selection of the emission wavelength, a second spectrometer arrangement identical to the first spectrometer arrangement, and a detector for acquiring the brightness distribution are arranged one behind another in an image beam path, an incoupling of excitation light being accomplished, backwards through the wavelength selection aperture, via an excitation beam path that leads from a source for monochromatic excitation light, through a strip aperture corresponding to the confocal strip aperture and a third spectrometer arrangement identical to the first spectrometer arrangement, to the wavelength selection aperture, the image beam path and the excitation beam path being coordinated with one another and constituted in such a way that light emitted from the specimen arrives via the wavelength selection aperture at the detector, but excitation light is prevented by the wavelength selection aperture from striking the detector but passes through the confocal strip aperture.

German Unexamined Application DE 198 42 288 A1 discloses an apparatus for adjustable detection of specimen light coming from an illuminated specimen, preferably in a microscope beam path, comprising at least one dispersive element for wavelength separation of the specimen light as well as means, arranged in the wavelength-separated portion of the specimen light, for adjustable blocking out of at least one wavelength region and deflection in the direction of at least one detector.

The known methods and apparatuses are of only limited suitability for spectral analysis of the light proceeding from a specimen and for the acquisition of entire spectra that are e.g. several tens or several hundreds of nanometers wide, and exhibit critical disadvantages for these applications. The apparatuses in which spectrometers, in particular grating spectrometers, are provided often have insufficient spectral resolution especially for fluorescence microscopy applications. This is usually attributable to unavoidable scattering of light at the grating structures. Apparatuses that contain prism spectrometers having downstream line detectors, for example photodiode arrays, exhibit insufficient dynamics in terms of detection sensitivity. The apparatuses that exhibit both good spectral resolution and good dynamics in terms of detection sensitivity, for example the apparatus known from the aforesaid German Patent DE 195 10 102 C2, are capable, however, of simultaneously detecting only a limited number of spectral regions to be defined by the user.

SUMMARY OF THE INVENTION

It is therefore the object of the invention to propose a method for spectral analysis of the light proceeding from a specimen that on the one hand offers the possibility of high spectral resolution and good sensitivity dynamics, and on the other hand makes possible rapid and efficient spectral analysis over a definable spectral region.

This object is achieved by way of a method for spectral analysis of the light proceeding from a specimen using a multi-band detector comprising the steps of:
 a) defining an overall spectral region;
 b) defining a first spectral subregion and defining at least a second spectral subregion; wherein the first spectral subregion and the second spectral subregion are in the overall spectral region,
 c) simultaneously detecting the light proceeding from the specimen in the first and the second spectral subregion, and generating detection values;
 d) displacing the first spectral subregion and displacing the second spectral subregion within the overall spectral region; and
 e) repeating steps c) and d) until the light has been detected over the entire overall spectral region.

A further object of the invention is to describe a scanning microscope that on the one hand offers the possibility of high spectral resolution and good sensitivity dynamics, and on the other hand makes possible rapid and efficient spectral analysis over a definable spectral region.

This object is achieved by way of a scanning microscope having a multi-band detector that detects light proceeding from a specimen in at least a first and a second spectral subregion, wherein the spectral regions are simultaneously displaceable.

The invention has the advantage that the light proceeding from a specimen can be analyzed in such a way as to make possible rapid and efficient acquisition of entire spectra with no need for the user to accept the disadvantages exhibited by spectrometers.

In a preferred embodiment, the method contains the further steps of generating a detected spectrum from the detection values, and displaying the detected spectrum. The detected spectrum is preferably displayed on the monitor or on the display of a PC. A false-color depiction is particularly illustrative in this context.

In very particularly advantageous fashion, the method is performed using a scanning microscope, in particular a confocal scanning microscope. It is precisely in scanning microscopy that the aforementioned advantages of the method and the scanning microscope according to the present invention are completely expressed.

In a preferred embodiment, the scanning microscope contains an apparatus having the features of claim 1 of DE 43 30 347 A1. As already set forth in the general description, an apparatus of this kind encompasses a means for spectral division of the light proceeding from the specimen and, subsequently, a mirror-stop arrangement that directs different components of the spectrally divided light to various detectors. In the embodiment according to the present invention, the individual mirror stops are simultaneously displaceable. Actuating motors that bring about the displacement of the mirror stops are preferably provided. In a very particularly preferred embodiment, the displacements are accomplished in computer-controlled fashion.

Since the dispersion of the means for spectral division, which can be embodied e.g. as a prism, is not linear, in a preferred embodiment provision is made for calibrating the multi-band detector and storing the calibration data in the memory of a PC or of a computer, so they can be taken into account upon displacement of spectral regions. In this manner, for example, the width of the spectral regions can be kept constant.

Since the detectors as a rule do not have exactly the same characteristics, discontinuities could occur upon assembly of the data measured in the various spectral regions. These discontinuities are avoided preferably by calibrating the sensitivity of the detectors, for example the high voltage of photomultipliers. An adaptation can be performed using measurements at the edge of the specimen. Firstly the overall spectral region is scanned in only one of the defined spectral regions in order to identify the wavelength region in which the greatest signal may be expected. A specific gray value (in the range 0–255) is defined therein. Then the other spectral regions are displaced sequentially to the same spectral position, and the sensitivities of the detectors (PMT high voltage) are matched to one another. Before the overall spectral region is displayed, a smoothing of the generated data is preferably provided for. This is accomplished in the PC.

The light can derive from a single scan point or a line or an area or a defined volume of the specimen.

In an embodiment, the specimen is illuminated with illuminating light of at least one wavelength. The illuminating light preferably has multiple wavelengths. A multi-line laser, or several individual lasers whose emitted light is combined into one illuminating light beam, can be provided as the light source. White light sources or light sources having a comb generator, for example made of photonic band-gap material, are also usable.

Dynamic processes can be examined with spectral resolution by line-wise or plane-wise switchover and simultaneous detection. When a plane of the specimen is being scanned in meander fashion, it is possible e.g. to illuminate the first, fourth, seventh, etc. line with illuminating light at a wavelength of 488 nm, the second, fifth, eighth, etc. line with illuminating light at a wavelength of 568 nm, and the third, sixth, ninth, etc. line with illuminating light at a wavelength of 633 nm, and to perform the displacement of the spectral region in each case after a specimen plane has been completely scanned.

In particular when the light proceeding from the specimen is fluorescent light, and when the illuminating light contains several different wavelengths in order, for example, to excite different dyes in the specimen, it is especially advantageous that spectral components of the illuminating light can be blocked out during detection in order to prevent illuminating light reflected from the specimen from being detected in addition to the fluorescent light. This is necessary whenever a displaced spectral subregion encompasses one of the illuminating wavelengths. The gap in detected information in another spectral subregion resulting from the brief blockage can be closed up at a time after the blockage.

In this context, a scanning microscope in which an acoustooptical component is provided for separation of the excitation and detection beam paths is of very particular advantage. An optical arrangement that is advantageously combinable with the scanning microscope according to the present invention is known from German Unexamined Application DE 199 06 757 A1. This optical arrangement contains at least one acoustooptical component for coupling the excitation light of at least one light source into the microscope and for blocking the excitation light or excitation wavelength scattered and reflected from the specimen out of the light coming from the specimen via the detection beam path. For variable configuration with a very simple design, the optical arrangement is characterized in that excitation light of differing wavelengths can be blocked out by means of the acoustooptical component. Alternatively, an optical arrangement of this kind is characterized in that the spectrally selective element can be set to the excitation wavelength that is to be blocked out.

In contrast to a dielectric main beam splitter for separation of the excitation and detection beam paths, which always exhibits a very particular transmission characteristic for the detected light and thus results in distortion of the emission spectrum, an acoustooptical component can be adapted almost ideally to the excitation and emission wavelengths. The acoustooptical component is almost completely transparent at all emission wavelengths, except that a spectral window of only approx. 2 nm is cut out for the excitation wavelengths. The excitation wavelength can be suppressed in the detection beam path so effectively that spectral regions can be placed almost in the immediate spectral vicinity of the excitation wavelength without allowing excitation light to enter the detectors.

In a preferred embodiment, definition of the spectral regions is accomplished automatically. Appropriate spectral subregions and appropriate displacement steps are determined by the PC from the data of a test measurement.

A variety of input devices can be provided as means for definition of an overall spectral region and as means for definition of the first and second spectral regions. The regions are preferably inputted using the computer mouse, by way of sliders displayed on the monitor of a PC. Definition of the spectral regions and of the overall spectral region encompasses definition of the spectral width and definition of the spectral location. By displacing the first and second spectral regions, the overall spectral region can be successively covered and the wavelength data can be acquired over the entire overall spectral region. In a preferred embodiment, the spectral regions are continuously displaceable.

BRIEF DESCRIPTION OF THE DRAWINGS

The subject matter of the invention is depicted schematically in the drawings and will be described below with reference to the Figures, identically functioning elements being labeled with the same reference characters. In the drawings.

DETAILED DESCRIPTION OF THE INVENTION

Figure 1:
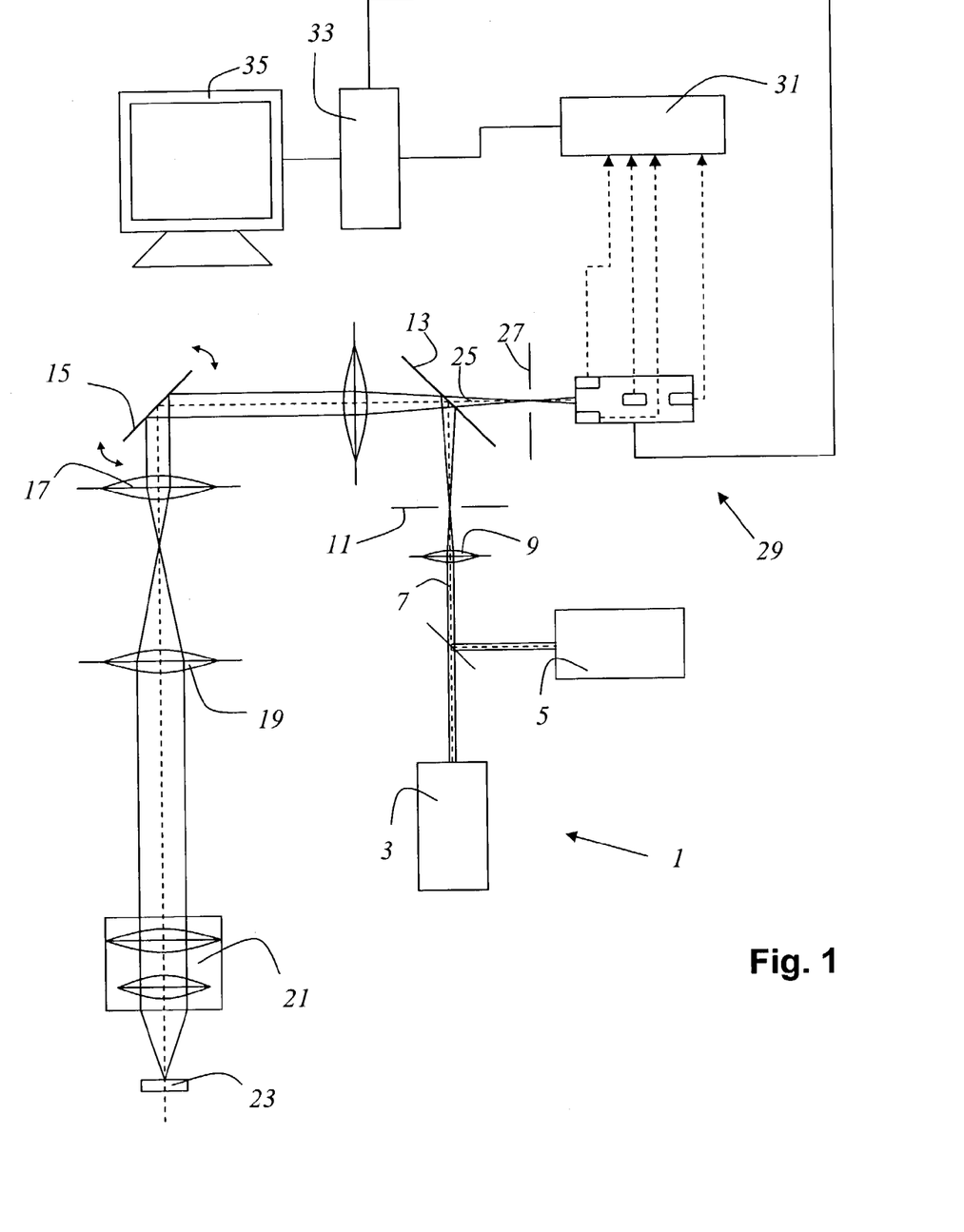
FIG. 1 shows a scanning microscope according to the present invention.

FIG. 1 schematically shows a scanning microscope according to the present invention that is embodied as a confocal scanning microscope. Illuminating light beam 7, from an illumination system 1 that comprises a first laser 3 and a second laser 5, contains four wavelengths. Illuminating light beam 7 is focused with the aid of optical system 9 onto the illumination pinhole. Illuminating light beam 7 travels via a beam splitter 13 to the gimbal-mounted scanning mirror 15, which guides illuminating light beam 7, through scanning optical system 17, tube optical system 19, and objective 21, over or through specimen 23. With non-transparent specimens 23, illuminating light beam 7 is guided over the specimen surface. With biological specimens 23 (preparations) or transparent specimens, illuminating light beam 7 can also be guided through specimen 23. This means that different focal planes of the specimen can be successively scanned by illuminating light beam 7. Subsequent assembly then yields a three-dimensional image of specimen 23. Light 25 proceeding from specimen 23 travels through objective 21, tube optical system 19, and scanning optical system 17 and via scanning mirror 15 to beam splitter 13, passes through the latter and, after passing through detection pinhole 27, strikes a multi-band detector 29. Multi-band detector 29 detects light 25 proceeding from the specimen in four previously defined spectral regions that are simultaneously displaceable, so that displacement of the spectral regions allows an overall spectral region of light 25 to be successively spectrally analyzed. Multi-band detector 29 generates electrical detected signals proportional to the power level of the light in the respective spectral regions, and forwards them to a processing unit 31. In processing unit 31, evaluation of the detected signals is accomplished. This includes, inter alia, the generation of detection values that are then forwarded to a PC 33. PC 33 generates, from the detection values, a complete detected spectrum of the overall spectral region previously defined by the user, and displays it in a coordinate system on a monitor 35. PC 33 also controls multi-band detector 29. For better clarity, certain optical elements for guiding and shaping the light beams are omitted from the Figure. These are sufficiently familiar to the person skilled in this art.

Figure 2:
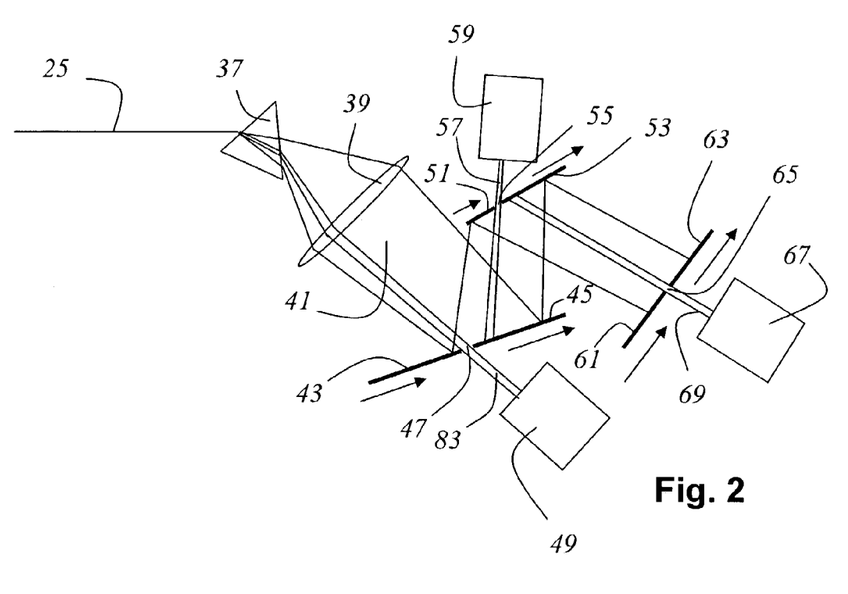
FIG. 2 shows an embodiment of the multi-band detector of the scanning microscope.

FIG. 2 shows a multi-band detector that detects light 25 proceeding from a specimen in three spectral regions, the spectral regions being simultaneously displaceable. Light 25 proceeding from a specimen is spectrally spread by a prism 37 and then focused by a lens. A first portion 39 of light fan 41 passes through first slit opening 47 formed by first mirror stop 43 and second mirror stop 45, and arrives at first detector 49. The remainder of the spectral fan is reflected by mirror stops 43, 45 and arrives at third and fourth mirror stops 51, 53, which form second slit opening 55. A second portion 57 of spectral fan 41 passes through second slit opening 55 to a second detector 59; the remaining light is reflected to a fifth and sixth mirror stop 61, 63 that form a third slit opening 65, through which a third portion 69 of spectral fan 41 arrives at a third detector 67. Mirror stops 43, 45, 51, 53, 61, 63 are displaceable in motor-driven fashion along the intersection line between the mirror plane and the spreading plane. The location and width of slit openings 47, 55, 65 define a first, second, and third spectral subregion; these spectral regions are displaceable by simultaneous displacement of mirror stops 43, 45, 51, 53, 61, 63, and the entire spectral fan is successively detectable as a whole. The displacement is performed in computer-controlled fashion.

Figure 3:
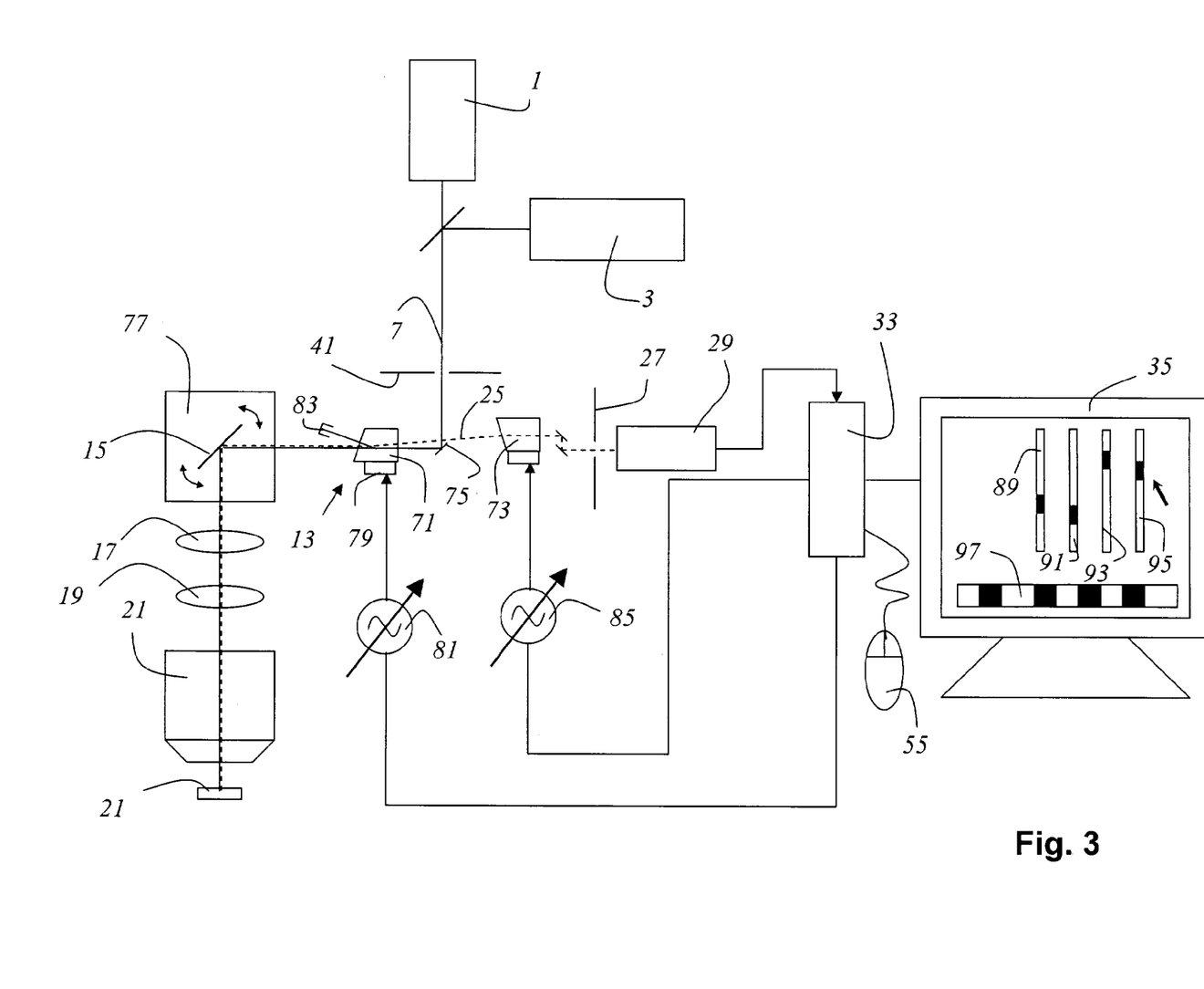
FIG. 3 shows a further scanning microscope.

FIG. 3 shows a scanning microscope according to the present invention in which beam splitter 13 shown in FIG. 1 is replaced by an acoustooptical component 71 that is embodied as an AOTF. Illuminating light beam 7 is reflected by a deflection mirror 75 to acoustooptical component 71. From acoustooptical component 71, illuminating light beam 7 travels through beam deflection device 77, which contains a gimbal-mounted scanning mirror 15 and which guides illuminating light beam 7, through scanning optical system 17, tube optical system 19, and objective 21, over or through specimen 23. Light 25 proceeding from the specimen passes through scanning optical system 17, tube optical system 19, and objective 21 in the opposite direction, and arrives via scanning mirror 15 at acoustooptical component 71, which conveys light 25 to a compensation element that is embodied as a further acoustooptical component 73. After passing through further acoustooptical component 73, light 25 strikes a mirror pair that directs light 25, after passing through detection pinhole 27, to multi-band detector 29. Acoustooptical component 71, which serves to select the portions of illuminating light beam 7 of the selected wavelengths, is configured as an AOTF through which an acoustic wave passes. The acoustic wave is generated by an electrically activated piezoacoustic generator 79. Activation is effected by a high-frequency source 81 that generates an electromagnetic high-frequency wave which has multiple settable HF frequencies. The HF frequencies are selected so that only the portions of illuminating light beam 7 of the desired wavelengths arrive at beam deflection device 77. The other portions of illuminating light beam 11, not influenced by the acoustic excitation, are deflected into a beam trap 83. Further acoustooptical component 73 is also embodied as an AOTF and is activated by a further high-frequency source 85 with a further electromagnetic high-frequency wave. The HF frequency of the further electromagnetic high-frequency wave is selected in such a way that those portions of light 25 proceeding from the specimen which exhibit the wavelength of illuminating light wave 7 are blocked out. A PC 33 is provided for selection of the HF frequencies. PC 33 controls high-frequency source 81 and further high-frequency source 85 and multi-band detector 29 as defined by the user. The user performs settings using computer mouse 87. A slider 89, 91, 93, 95 that serves to set the amplitude is displayed on monitor 35 for each selected HF frequency. Also provided on the monitor is a further slider 97 for defining the width and initial position of the spectral regions. Each spectral subregion is represented, within the slider, by a block of adjustable width that can be displaced as a whole.

Figure 4:
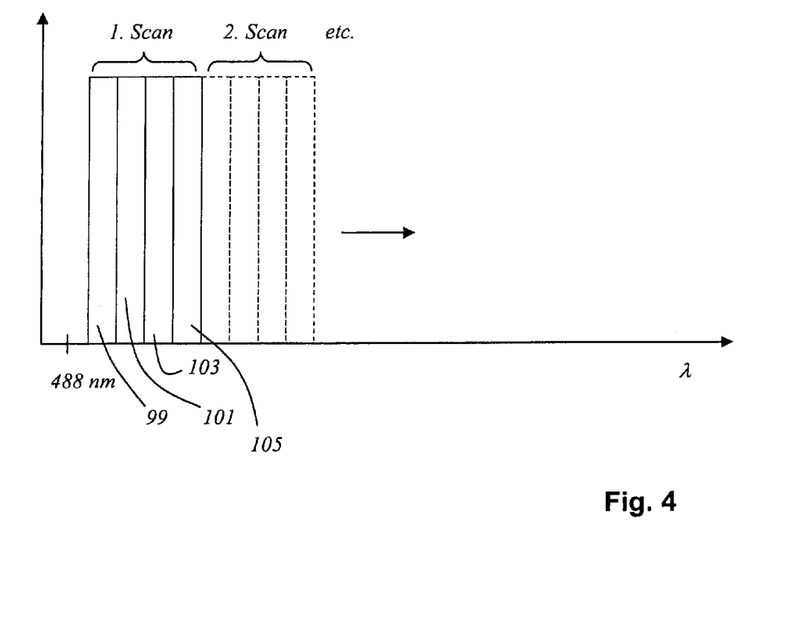
FIG. 4 shows a variant embodiment of the method.

FIG. 4 illustrates an embodiment of the method. The intention is to spectrally analyze the fluorescent light of a specimen that is being excited with illuminating light at a wavelength of 488 nm. To begin, the four available spectral regions 99, 101, 103, 105 are defined. First spectral subregion 99 is 10 nm wide and extends from 495 nm to 505 nm. Second spectral subregion 101 extends from 505 nm to 515 nm, third spectral subregion 103 from 515 nm to 525 nm, and fourth spectral subregion 105 from 525 to 535 nm. After the first scan of the specimen, spectral regions 99, 101, 103, 105 are simultaneously displaced 40 nm, and the second scan begins; and so forth.

Figure 5:
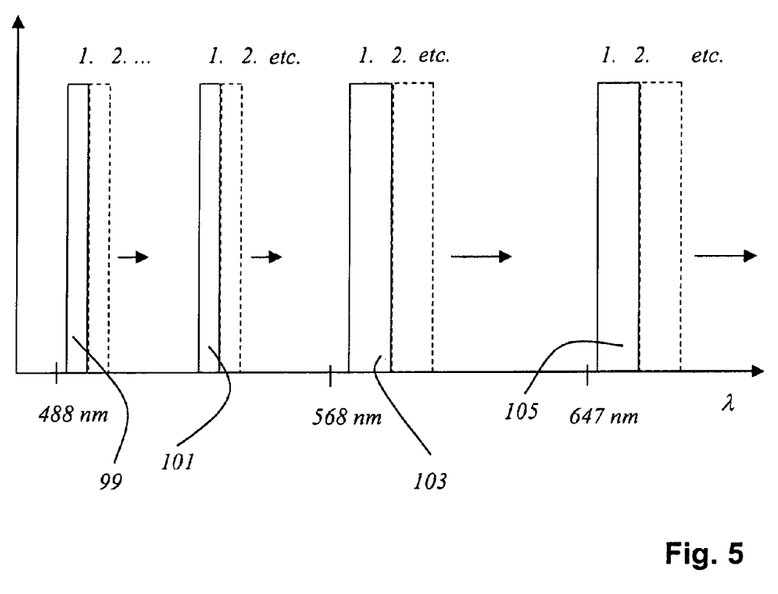
FIG. 5 shows another variant embodiment of the method.

FIG. 5 illustrates an embodiment of the method. The intention is to spectrally analyze fluorescent light of a specimen that is being excited with illuminating light at wavelengths of 488 nm, 568 nm, and 747 nm. To begin, the four available spectral regions 99, 101, 103, 105 are defined. First spectral subregion 99 is 5 nm wide and extends from 495 nm to 500 nm. Second spectral subregion 101 extends from 530 nm to 535 nm, third spectral subregion 103 from 570 nm to 580 nm (10 nm wide), and fourth spectral subregion 105 from 655 to 665 nm. After the first scan of the specimen, spectral regions 99, 101, 103, 105 are simultaneously displaced by an amount equal to their respective widths. The first and second are each displaced 5 nm, and the third and fourth each 10 nm; then the second scan begins, and so forth.

The invention has been described with reference to a particular exemplary embodiment. It is self-evident, however, that changes and modifications can be made without thereby leaving the range of protection of the claims below.

What is claimed is:

1. A method for spectral analysis of the light proceeding from a specimen using a multi-band detector comprising the steps of:
   a) defining an overall spectral region;
   b) defining a first spectral subregion and defining at least a second spectral subregion;
   wherein the first spectral subregion and the second spectral subregion are in the overall spectral region;
   c) scanning the specimen with illuminating light using a scanning microscope;
   d) simultaneously detecting detection light proceeding from the specimen in the first and the second spectral subregion, and generating detection values;
   e) displacing the first spectral subregion and displacing the second spectral subregion within the overall spectral region; and
   f) repeating steps d) and e) until the detection light has been detected over the entire overall spectral region.

2. The method as defined in claim 1, comprising the further steps of:
   generating a detected spectrum from the detection values; and
   displaying the detected spectrum.

3. The method as defined in claim 2, wherein the displaying of the detected spectrum contains a false-color depiction.

4. The method as defined in claim 1, wherein the displacing the first and second spectral subregions is performed so as to simultaneously displace the first and second spectral subregions.

5. The method as defined in claim 1, wherein the light derives from a single scan point or a line or an area of the specimen.

6. The method as defined in claim 1, wherein the detection light proceeding from the specimen is fluorescent light.

7. The method as defined in claim 1, wherein spectral portions of the illuminating light are blocked out during detection.

8. The method as defined in claim 6, wherein spectral portions of the illuminating light are blocked out during detection.

9. The method as defined in claim 1, wherein definition of the spectral regions is accomplished automatically.

10. A scanning microscope comprising:
    an illuminating light source configured to illuminate a specimen;
    a scanning device configured to scan the specimen with the illuminating light;
    a multi-band detector configured to simultaneously detect detection light proceeding from the specimen in at least a first and a second spectral subregion; and
    a spectral subregion defining device configured to displace the first and second spectral subregions.

11. The scanning microscope as defined in claim 10, wherein the spectral subregion defining device is configured to displace the first and second spectral subregions so as to detect the detection light over an overall spectral region.

12. The scanning microscope as defined in claim 10, wherein the spectral subregion defining device is configured to define the first and second spectral subregions from an overall spectral region.

13. The scanning microscope as defined in claim 10, wherein the spectral subregion defining device is configured to operate automatically.

14. The scanning microscope as defined in claim 10, wherein the spectral subregion defining device is configured to continuously displace the first and second spectral regions.

15. The scanning microscope as defined in claim 10, wherein the multi-band detector comprises at least one movable mirror stop.

16. The scanning microscope as defined in claim 10, wherein the scanning microscope has an excitation beam path and a detection beam path, an acoustooptical component being provided for separation of the excitation and detection beam paths.

17. The scanning microscope as defined in claim 10, wherein the spectral subregion defining device is configured to simultaneously displace the first and second spectral subregions.

* * * * *